United States Patent [19]

La Motte, III et al.

[11] Patent Number: 4,493,896
[45] Date of Patent: Jan. 15, 1985

[54] DUAL CHAMBER MICROPLATE WASHER

[75] Inventors: George B. La Motte, III, Larkspur; Samuel Burd, Oakland, both of Calif.

[73] Assignee: Bio-Rad Laboratories, Inc., Calif.

[21] Appl. No.: 434,309

[22] Filed: Oct. 14, 1982

[51] Int. Cl.³ .................. C12M 1/00; C12M 1/32; B01L 3/00

[52] U.S. Cl. .................. 435/287; 435/293; 422/99; 73/863.32

[58] Field of Search .................. 435/30, 287, 291, 292, 435/293; 422/63, 99, 100; 134/21, 22, 18, 102, 172, 174, 198; 141/89, 91, 92; 73/863.32

[56] References Cited

U.S. PATENT DOCUMENTS

| | | | |
|---|---|---|---|
| 3,261,208 | 7/1966 | Fisher | 73/863.32 |
| 3,536,449 | 10/1970 | Astle | 73/863.32 X |
| 3,568,735 | 3/1971 | Lancaster | 422/100 X |
| 3,609,040 | 9/1971 | Kuzel et al. | 435/30 X |
| 3,650,306 | 3/1972 | Lancaster | 422/100 X |
| 3,881,872 | 5/1975 | Naono | 134/21 X |
| 3,949,771 | 4/1976 | Dodge et al. | 134/174 X |
| 4,098,305 | 7/1978 | Gates | 141/92 |
| 4,227,886 | 10/1980 | Bullock et al. | 134/18 X |
| 4,236,825 | 12/1980 | Gilford et al. | 356/414 |
| 4,245,042 | 1/1981 | Weinstein et al. | 435/30 |
| 4,265,855 | 5/1981 | Mandle et al. | 422/63 X |

OTHER PUBLICATIONS

"Dynawasher II 96 Channel Washer/Aspirator Operating Instructions" from Dynatech Laboratories, Inc., Arlington, Va.
Pages 6 & 7 of catalog pages "Miniwash Washer-Aspirator" and Dynawasher II & Dynadrop TM Sr.
"Product Information/Titertek® Multiwash", Flow Laboratories, Inc. (1981) (3 unnumbered pages).
"Product Information/Titertek® Autodrop", (1981, Flow Laboratories, Inc.).

Primary Examiner—David M. Naff
Assistant Examiner—Randall E. Deck
Attorney, Agent, or Firm—Townsend and Townsend

[57] ABSTRACT

A novel apparatus is disclosed for the alternate filling and evacuation of all wells simultaneously of a multi-well microplate. The apparatus consists of a flat, horizontally disposed distribution head comprised of an upper and a lower chamber formed by these parallel plates, with a rectangular array of tubes passing through the lower of the three plates such that two tubes are aligned with each well of a microplate, one for filling and the other for evacuation. The filling tubes and evacuation tubes extend below the lower plate for unequal distances, the evacuation tubes being the more extended. All filling tubes communicate with one of the two chambers in the distribution head, while all evacuation tubes communicate with the other. The microplate is supported below the distribution head with the tubes in proper alignment, and means are provided for bringing the microplate and the tubes in close proximity, for applying a vacuum to the chamber communicating with the evacuation tubes, and for supplying pressurized wash fluid to the chamber communicating with the filling tubes. The apparatus provides a faster washing process for microplates, and is more reliable and efficient than devices already known for the same or similar purposes.

8 Claims, 2 Drawing Figures

DUAL CHAMBER MICROPLATE WASHER

BACKGROUND OF THE INVENTION

I. Field of the Invention

A critical processing step in many genetic engineering and molecular biology techniques is the selection of a particular cell or cell colony from a multitude of similar species. Hybridoma technology, where the fusion and plating of hybrid cells generally results in several thousand clones is one example of a process requiring such selection. The clones are typically screened by immunoassay techniques to select the single clone producing the specific antibody of interest. To preserve the activity of the cells, the screening must take place within a few days. Screening is generally accomplished by the use of a series of microplates, each containing a large number of wells, each well designed to accommodate a single clone.

Screening techniques involving microplates generally involve two or more steps in each of which a reagent or reagent mixture is added to each well. For reliability and accuracy of results, the wells must be emptied between these steps, and rinsed with a washing solution to eliminate non-specifically bound reagents. It is often necessary to rinse and evacuate each of the wells in a large number of microplates several times within the course of a single screening procedure.

The present invention relates to an apparatus for the washing of all wells in a microplate at once, in a highly efficient and reliable manner.

II. Description of the Prior Art

A variety of microplate washers are commercially available. A manual device known as the "Miniwash Washer-Aspirator" is available from Dynatech Laboratories, Inc., Arlington, Virginia. This device is hand-operated, and capable of filling and evacuating only one row (eight wells) of a microplate at one time. A thorough wash of an entire microplate takes several minutes, and the likelihood of spillage from one well to an adjacent well is a serious disadvantage. A further manually-operated device is the "Dynawasher II", also available from Dynatech Laboratories, Inc. Although this device is designed to handle all wells in a microplate simultaneously, it has two positions, located at the extreme ends of a horizontal track, one for aspiration and the other for filling the wells with wash fluid. Finally, an automatic device bearing the name "Titertek ® Multi-Wash" is available from Flow Laboratories, Inc., McLean, Virginia. This device is capable of washing and filling only two rows of a microplate at a time. The mechanism is completely enclosed, precluding detection by the operator of such problems as incomplete filling or aspiration of the wells, both of which are known to plague this instrument.

SUMMARY OF THE INVENTION

An apparatus is provided for the alternate filling and evacuation of all wells simultaneously of a multi-well microplate. By virtue of its low cost, simple construction, versatility, and efficiency of operation, the apparatus of the invention overcomes the disadvantages of the prior art and offers a reliable and effective means for washing a large number of microplates in a relatively short period of time. The speed and efficiency of screening processes in multiple assay procedures is thus considerably enhanced.

The apparatus consists in general of a flat, horizontally disposed distribution head comprising three parallel plates spaced apart to form gaps defining an upper and lower chamber, the middle plate forming a common boundary between the two chambers. A rectangular array of tubes passes through the lower plate and is arranged such that a pair of tubes is aligned with each well of a microplate. One of the tubes of each pair serves as a filling tube and the other an evacuation tube, the former providing an open passage with one of the chambers, and the latter providing an open passage with the other. The distribution head is positioned above a support surface parallel to the plates, and contains guide means to secure the microplate in position such that each well is in alignment with a single pair of tubes. Means are provided for narrowing and widening the gap between the distribution head and the microplate, as well as means for applying a vacuum to the chamber in communication with the evacuation tubes and for supplying pressurized wash fluid to the chamber in communication with the filling tubes.

A further understanding of the invention will be facilitated by reference to the attached drawings.

DETAILED DESCRIPTION OF THE DRAWINGS

Figure 1:
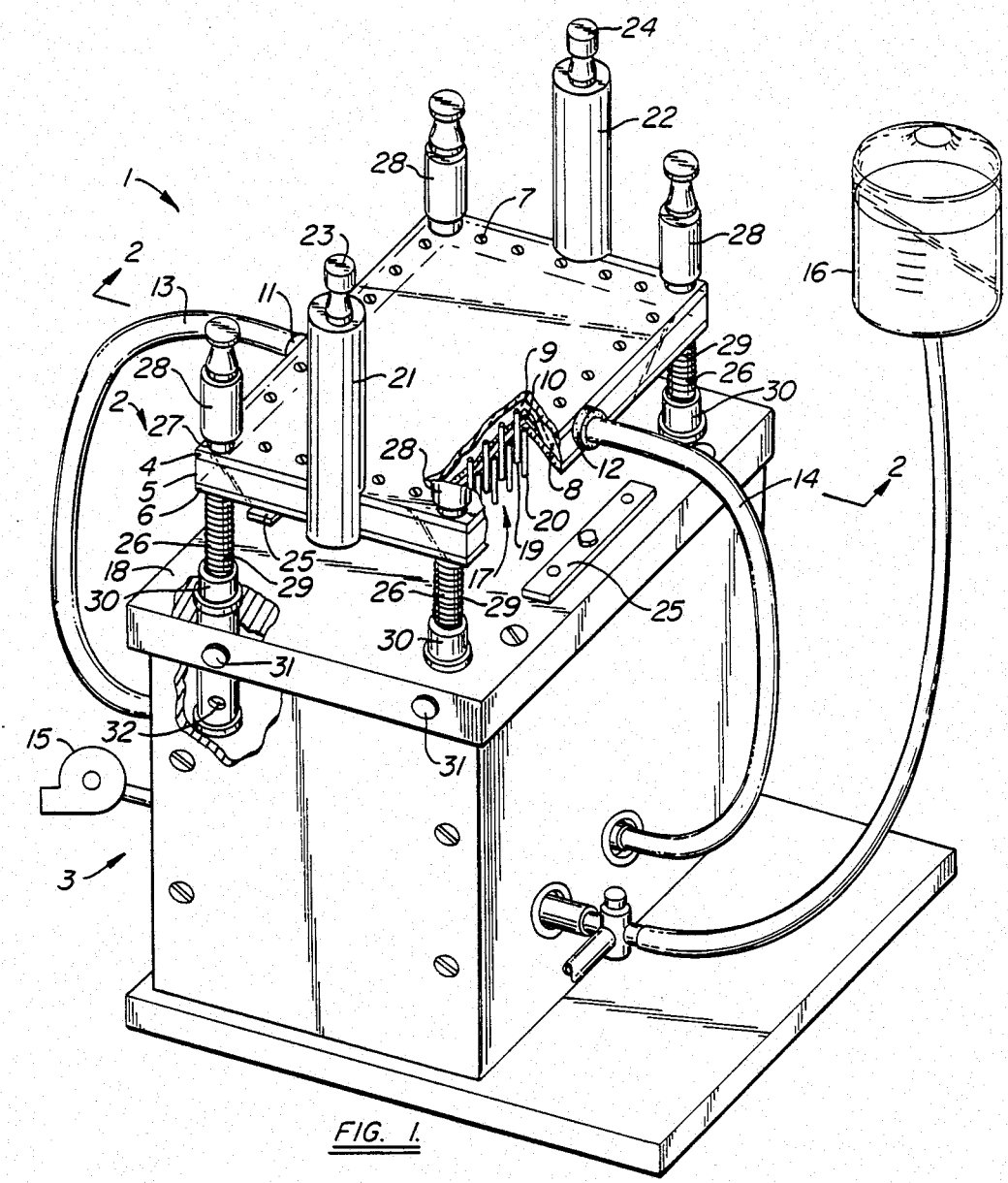
FIG. 1 is a perspective view of one embodiment of the apparatus of the present invention.

FIG. 1 illustrates a filling/evacuating apparatus 1 constituting one embodiment of the present invention. The apparatus consists of a flat horizontal distribution head 2 mounted above a support 3 to permit a vertical translational movement of one with respect to the other, and with sufficient space in between to accommodate and permit the easy removal of a microplate.

The distribution head is defined by three parallel plates, an upper 4, a middle 5, and a lower 6, all secured together in fluid-tight manner by securing screw 7. The middle plate 5 is milled on both sides so that only its periphery 8 is in contact with the upper and lower plates. The three plates thus form an upper chamber 9 and a lower chamber 10 with a common wall formed by middle plate 5. The middle plate is further drilled to accommodate tubing connections 11 and 12, the former communicating with the upper chamber 9 and the latter with the lower chamber 10. The tubing connections are fitted to conduits 13 and 14, one of which connects to a vacuum source 15 through a valve or switching mechanism (not shown), while the other connects to a source of pressurized fluid supply 16 through a second valve or switching mechanism (also not shown). These switches can each be conveniently located in the interior of the microplate support base 3, and are conveniently operated by an accessible control.

Any conventional vacuum source, such as pumps, aspirators, etc., can be used. The degree of vacuum is not critical, provided that it is sufficient to effect evacuation from all wells of the microplate within a reasonable period of time. In most applications, a vacuum of at least about ten inches (25.4 cm) of mercury will be most convenient, preferably at least about twenty inches (50.8 cm). Likewise, any conventional means of pressurizing the feed fluid can be used. The degree of pressurization is not critical, provided that it is sufficient to effect the filling of the wells at a controllable rate. This will depend to some extent on the size of the tubes (discussed below) and the viscosity of the fluid. Normally, any slight head will suffice. In most applications, a head of at least about one foot (30 cm) of water will provide the best results, preferably at least about three feet (92 cm).

Passing through the lower plate 6 of the distribution head are a series of tubes 17 arranged in a rectangular array. The tubes are spaced such that two such tubes are aligned with each well of a microplate when the latter is resting on the upper surface 18 of the support 3. The tubes are of sufficient number to include one pair for each microplate well. Since most microplates contain 96 wells, arranged in twelve rows of eight each, the preferred number of tubes is 192. Typical 96-well microplates have a well spacing of approximately 9mm, center-to-center. Each pair of tubes, therefore, is spaced approximately 9mm from the next. The two tubes of each pair are sufficiently close to each other to both come within each well perimeter, yet far enough apart to prevent a direct flow path from one to the other.

Each of the tubes 17 extends a short distance below the lower plate 6. The two tubes in each pair, designated hereinafter as a filling tube 19 and an evacuation tube 20, respectively, extend for unequal distances below the lower plate 6, the filling tube being the less extended, and the evacuation tube the more extended. The length of each tube is sufficient to extend into the microplate wells when the distribution head 2 is lowered to its lowermost position. A convenient length is on the order of one inch (2.54 cm) or less, preferably about one-half inch (1.27 cm). The difference in length between the two tubes is preferably less than the depth of each well. The purpose of the difference in length is to optimize the filling and evacuation functions of the tubes—i.e., when the apparatus is in operation, the evacuation tubes will be lowered so that their lower ends are sufficiently close to the bottom of the well to permit evacuation of substantially all the liquid from the well, whereas the filling tube will terminate at a sufficient height above the bottom of the well to permit filling of the well with a minimum of splashing and flow obstruction. For most wells, a length difference ranging from about 0.05 inch (0.127 cm) to about 0.4 inch (1.02 cm) is appropriate.

All tubes of a single function (i.e., evacuation or filling) are of appropriate length and position to provide an open flow passage between the lower-most opening of the tube and the interior of one of the two distribution head chambers. All tubes of the remaining function similarly provide an open flow passage between their lowermost openings and the interior of the other chamber. In the embodiment shown in the drawings, the evacuation tubes 20 communicate with the lower chamber 10, while the filling tubes 19 communicate with the upper chamber 9. Consequently, the lower chamber 10 is the chamber to which the vacuum source 15 is engaged through conduit 13 and fitting 11, and the upper chamber 9 is the one to which the source of pressurized fluid 16 is engaged through conduit 14 and fitting 12.

The tubes may terminate at their upper end either in the plate forming the lower boundary of the corresponding chamber, or alternatively may extend a short distance above the plate forming the lower boundary to terminate within the interior of the chamber. In the embodiment shown in FIG. 2, the former alternative is exemplified by the evacuation tubes 20 which terminate in the lower plate 6, and the latter is exemplified by the filling tubes 19 which extend into the upper chamber 9. Ths configuration is preferred since it provides a reservoir below the upper tips of the filling tubes for the liquid to rest while bubbles generated during transfer are permitted to escape prior to the passage of the fluid down through the filling tubes into the microplate wells situated below the distribution head. All tubes are sealed in fluid-tight manner in the plates through which they pass, so that all possibility of leakage between the two chambers is avoided. Solvent bonding is a convenient and effective method of achieving such a seal.

The support 3 is comprised of any structure capable of forming a flat horizontal surface 18 to hold a microplate. In the embodiment shown in FIG. 1, the support is an enclosed structure, which houses the valves or switching means governing the flow of pressurized wash fluid to the filling tubes and the access to the vacuum source. Solenoid valves are particularly useful as switching means for both functions, and an enclosed structure such as that shown, which houses the solenoids, is particularly efficient, and thus preferred. Control switches for the solenoids can be located at any convenient location provided they are accessible to the operator. In the drawing, the switches are mounted atop posts 21 and 22 extending upward from the vacuum changer. Switch 23 controls the valve on the pressurized fluid line and is activated for the wash step, and switch 24 controls the valve on the vacuum line and is activated for the evacuation step.

Attached to the microplate support surface 13 are guide means 25 for fixing the position of a microplate. Since microplates are generally of rectangular configuration, the guide means will typically consist of three protrusions with straight edges (along the inside of each), positioned to abut three sides of the microplate (only two are visible in FIG. 1), with the fourth side (shown as the forward end) left open to permit easy placement and removal of the microplate by sliding the plate along the surface 18. The protrusions are shown as flat bars in the drawing, and can be either part of the surface 18, separate pieces permanently attached to the surface (as shown), or separate pieces attached in an adjustable manner so that their spacing can be modified to accommodate microplates of different dimensions. In any case, the guide means are positioned to secure each well of the microplate beneath a corresponding pair of filling and evacuation tubes.

The position of the distribution head 2 above the support surface 18 is fixed by any conventional means which will prevent motion in the horizontal direction. The embodiment shown in the drawing consists of four posts 26, one at each corner of the chamber. The posts are mounted rigidly on the support 3, but pass through the distribution head 2 through holes 27 to align the distribution head above the support such that the upper, middle and lower plates of the distribution head and the support surface are parallel to one another yet with a fit sufficiently loose to permit the distribution head 2 to slide down the posts 26 when posts 21 and 22 are grasped by an operator and pushed downward. Upward mobility of the distribution head is limited by an upper section 28 of each post which has a widened diameter which exceeds that of the opening 27 in the distribution head. Downward mobility is controlled by springs 29 around each post.

The distribution head is thus movable and the support surface 18 is stationary in the embodiment shown in FIG. 1. In an alternative embodiment, the distribution head itself is rigidly affixed to the support 3 and the surface 18 is movable.

In either embodiment, stop means 30 are provided for setting a minimum distance between the lower plate 6 of the distribution head and the microplate support surface 18. For efficient operation of the apparatus, the minimum distance is set to bring the exposed end of each evacuation tube sufficiently close to the bottom of the microplate well over which it is aligned to permit efficient evacuation of substantially all of the liquid from each well. Preferably, the stop means are adjustable so that wells of different depths can be accommodated. The stop means can be affixed to either the lower plate 6 of the distribution head, the posts 26, or the microplate support surface 18. In the embodiment shown in the drawing, the stop means 30 are affixed to the posts 26. Any configuration, however, which sets a minimum distance can be used. The construction of the apparatus can be designed to accommodate additional means of height adjustment, such as the peg inserts 31. These pegs are capable of securing the posts 26 in either of a plurality of fixed positions, as determined by the positions of holes passing transversely through each post. In the cutaway section at the left of FIG. 1, the lower hole 32 of two such holes is visible.

The materials of construction to be used in the apparatus of the invention are not critical, and can vary widely. Preferably, non-corrosive materials are used since the wash solution is frequently a saline solution. The filling and evacuation tubes may conveniently be constructed from small bore metal tubing, preferably stainless steel of the 18-8 series. The size of the tubing is likewise non-critical, but is preferably small enough to readily permit the filling of the wells by discrete drops when pressure is applied to the bubble chamber. Tubing of a size on the order of approximately 18 gauge is the most convenient.

It is further preferred that transparent materials be used for the distribution head. This will permit plugs to be more easily discerned, and facilitate the avoidance of air bubbles. Plastics and similar materials are useful in this regard.

Figure 2:
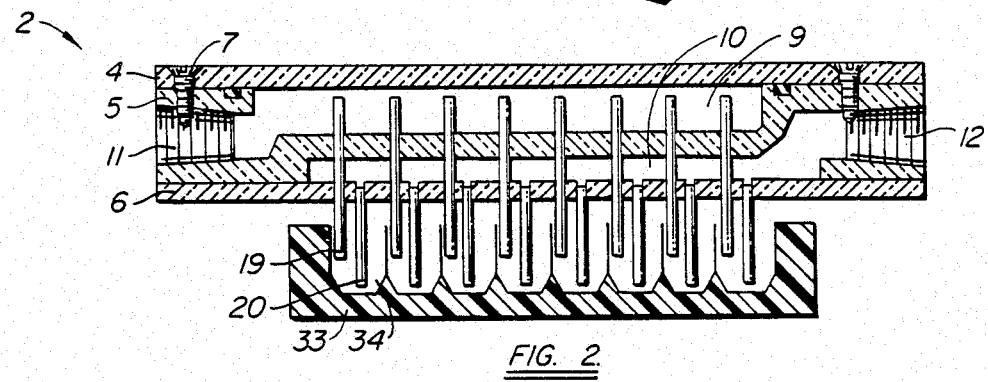
FIG. 2 is a sectional view of the distribution head and one row of filling and evacuation tubes, taken along Line 2—2 of FIG. 1.

In FIG. 2, a typical cross-sectional arrangement of the distribution head 2 of FIG. 1 is shown, taken along line 2—2 of FIG. 1. The evacuation tubes 20 and the filling tubes 19 are shown with the microplate 33 in position. One filling tube and one evacuation tube are aligned with each well 34 of the microplate. The lower end of the evacuation tube is positioned very close to the bottom of the well so that substantially complete evacuation is achieved.

At the option of the manufacturer, further features can be incorporated into the design to insure complete washing and evacuation without back spillage of wash fluid. As one example, a switch controlling the vacuum solenoid can be installed for activation by the upward movement of the distribution head 2 (or the lowering of the support surface 18 for embodiments where the distribution head is immovable). This will prevent backward spillage from the vacuum chamber into the wells in the event of jostling of the apparatus when the vacuum chamber is lifted. A magnetic reed switch or Hall effect switch is suitable for this purpose.

Finally, although operation of the filling and evacuation functions of the apparatus can be manually controlled as shown, a further variation would be the use of a microprocessor or similar device to program the functions for automated operation.

The foregoing description is offered solely for purposes of illustration; the invention is not intended to be limited to the particular features of construction and operation shown or described. Numerous modifications and variations of the above still falling within the spirit and scope of the invention as claimed hereinbelow will be readily apparent to those skilled in the art.

What is claimed is:

1. An apparatus for the filling and evacuation of all wells simultaneously of a multiwell microplate, said apparatus comprising:

a distribution head comprising three parallel plates designated, respectively, an upper plate, a middle plate, and a lower plate, said plates spaced apart to form gaps therebetween and thereby define two enclosed chambers designated, respectively, an upper chamber and a lower chamber with said middle plate forming a common boundary therebetween, said lower plate having affixed therein a plurality of tubes spaced apart from each other, each said tube passing through said lower plate and perpendicular thereto, said tubes forming a rectangular array such that, when said distribution head is superimposed over said microplate, a pair of said tubes is aligned with each well of said microplate, the portions of each tube of said pair which extends below said lower plate being of unequal length thereby defining a more extended tube and a less extended tube, said less extended tube extending upward through said lower chamber and said middle plate to terminate above the upper surface of said middle plate inside the interior of said upper chamber, and said more extended tube providing an open passage from its lower end to the interior of said lower chamber, a support for said microplate, said support comprising a substantially flat horizontal surface containing guide means adapted to secure said microplate in a predetermined position on said support surface, means for aligning said distribution head above said support with said upper, middle, and lower plates of said distribution head and said support surface in parallel relation, and for narrowing and widening the distance between said distribution head and said support surface while substantially maintaining said parallel relation, stop means for setting a minimum spacing distance between said distribution head and said support surface such that when said distance is at said minimum, the exposed end of the more extended tube of each said tube pair is sufficiently close to the bottom of the corresponding well in said microplate to permit evacuation of substantially all liquid from said well, means for applying a vacuum to said chamber communicating with said more extended tube, and means for supplying pressurized fluid to the chamber communicating with said less extended tube.

2. An apparatus according to claim 1 in which the difference in the length by which the tubes in each said tube pair extend below said lower plate is less than the depth of said well.

3. An apparatus according to claim 1 in which said guide means on said support surface are adjustable to accommodate microplates of different lateral dimensions.

4. An apparatus according to claim 1 in which said stop means are adjustable to accommodate microplates of different thicknesses.

5. An apparatus according to claim 1 in which said support surface is fixed and said distribution head is movable in the vertical direction, and said narrowing and widening of said distance between said distribution head and said support surface is achieved by lowering and raising said distribution head, respectively.

6. An apparatus according to claim 1 in which said upper, middle, and lower plates of said distribution head are transparent.

7. An apparatus according to claim 1 in which the number of tubes amounts to one said pair for each well of a 96-well microplate.

8. An apparatus according to claim 1 further comprising switching means for individually engaging each of said vacuum means and said pressurized fluid supplying means with the chamber communicating with the more extended tube and the chamber communicating with the less extended tube, respectively.

* * * * *